__United States Patent__ [19]

Schwarz

[11] 4,094,796
[45] June 13, 1978

[54] PROCESS FOR PREPARING NOVEL COMPOUNDS FOR USE AS FABRIC SOFTENERS IN WATER SOLUTIONS THEREOF

[75] Inventor: Eckhard C. A. Schwarz, 115 N. Park Ave., Neenah, Wis. 54956

[73] Assignee: Biax-Fiberfilm Corporation, Neenah, Wis.

[21] Appl. No.: 804,232

[22] Filed: Jun. 7, 1977

[51] Int. Cl.² .......................................... D06M 13/34
[52] U.S. Cl. ..................................... 252/8.8; 8/115.6; 252/8.9; 560/88; 560/196
[58] Field of Search ................. 252/8.8, 8.9; 260/404.8; 560/196, 88; 8/115.6

[56] References Cited

U.S. PATENT DOCUMENTS

| | | | |
|---|---|---|---|
| 2,679,511 | 5/1954 | De Groote | 560/196 |
| 2,679,514 | 5/1954 | De Groote | 560/196 |
| 3,009,884 | 11/1961 | Monson et al. | 252/357 |
| 3,348,968 | 10/1969 | Hulbert et al. | 252/8.9 |
| 3,595,813 | 7/1971 | Hartgrove | 8/115.6 |

*Primary Examiner*—William E. Schulz
*Attorney, Agent, or Firm*—Marn & Jangarathis

[57] ABSTRACT

There is disclosed a compound having the following structural formula:

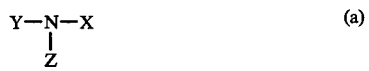

(a)

wherein X, Y, and Z each being selected from the group consisting of

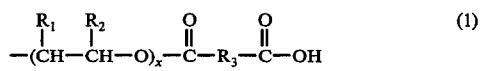
(1)

wherein one of $R_1$ and $R_2$ is hydrogen and the other is an alkyl group having from 1 to 6 carbon atoms with the alkyl to hydrogen mole ratio being less than 0.4 and X being an integer of at least 1 and $R_3$ is a diradical selected for the group consisting of $R_3$ is a diradical of either:
(a) 1 to 6 methylene groups
(b) a diradical of: —CH=CH—
(c) a diradical of:

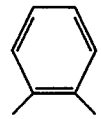

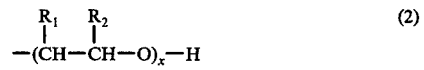

(2)

where $R_1$, $R_2$ and X are as defined above
alkyl radicals having from 1 to 6 carbon atoms

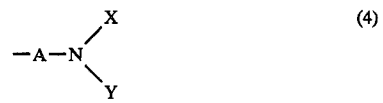
(4)

wherein
A is an alkylene radical having from 1 to 6 carbon atoms and X and Y are as defined above
wherein at least one of X, Y and Z has structural formula (1) and

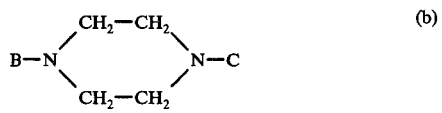
(b)

wherein B & C are each selected for the group consisting of radicals having above structural formula (1), above structural formula (2) and alkyl group having from 1 to 6 carbon atoms with at least one of B & C having structural formula (1).

A water solution of an effective amount of such compound exhibits excellent fabric softening properties. Such compound is formed by reacting polyoxyalkalene triamine compounds with an alkyloxy hydrocarbon under mild processing conditions.

11 Claims, No Drawings

PROCESS FOR PREPARING NOVEL COMPOUNDS FOR USE AS FABRIC SOFTENERS IN WATER SOLUTIONS THEREOF

BACKGROUND OF THE INVENTION

This invention relates to a group of novel polyoxyalkylene polymeric compounds having superior antistatic properties, and more particularly to a method of forming such compounds and the use of a water solution of an effective amount of such compounds as fabric softeners.

The art of producing surface active agents is old and well-developed, and it is a well-recognized principle that all such compounds are relatively large molecules which contain both hydrophobic and hydrophilic elements. The essential hydrophobic element in the prior art surface active agents has always been a hydrocarbon radical, such as found in the long chain fatty acids and alcohols, or in the alkylaryl group of the popular alkylaryl-sulfonate type detergents. The hydrophilic element has frequently been a polyoxyethylene chain, such as found in nonylphenolethylene oxide condensation products.

Polyoxyalkylene compounds prepared in accordance with U.S. Pat. No. 3,674,619 exhibit outstanding detergent and surface active properties. Numerous polyoxyalkylene triamine compounds are sold by BASF Wyandatte under the trademark "Tetronic" together with a number, such as 707, indicating percentage of ethylene oxide contained therein as well as an indication of the propylene oxide content thereof. Such polyoxyalkylene triamine compounds do not exhibit satisfactory antistatic properties since such compounds do not migrate to the fabric. In U.S. Pat. No. 3,009,884, there is disclosed the reaction of a polyoxyalkylene triamine with a dibasic acid or anhydride at 150° C. for at least one hour to form water insoluble resins used as oil-in-water demulsifier.

Objects of the Invention

An object of the present invention is to provide a novel fabric softener precursor.

Another object of the present invention is to provide a novel fabric softener which is more mild to the skin compared with conventional surface active agents.

Still another object of the present invention is to provide a novel fabric softener which is milder to clothes.

A still further object of the present invention is to provide a novel fabric softener which is not degradable.

A further object of the present invention is to provide a novel process for condensing polyoxyalkylene triamine compounds under conditions to form novel compounds where water solution of an effective amount thereof exhibits excellent fabric softening properties.

Summary of the Invention

These and other objects of the present invention are obtained by reacting polyoxyalkylene triamine compounds with alkyloxy hydrocarbons under mild processing conditions to react at least about 60 percent of the —OH groups of the polyoxyalkylene triamine compounds with the alkyloxy hydrocarbons to form a compound having the following structural formula:

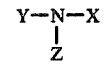 (a)

wherein X, Y, and Z each being selected from the group consisting of

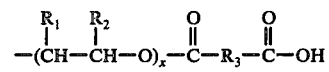 (1)

wherein one of $R_1$ and $R_2$ is hydrogen and the other is an alkyl group having from 1 to 6 carbon atoms with the alkyl to hydrogen mole ratio being less than 0.4 and X being an integer of at least 1 and $R_3$ is a diradical selected for the group consisting of $R_3$ is a diradical of either:
(a) 1 to 6 methylene groups
(b) a diradical of: —CH=CH—
(c) a diradical of:

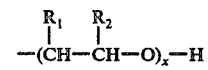 (2)

where $R_1$, $R_2$ and X are as defined above
(3) alkyl radicals having from 1 to 6 carbon atoms

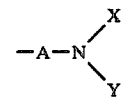 (4)

wherein
A is an alkylene radical having from 1 to 6 carbon atoms and X and Y are as defined above
wherein at least one of X, Y and Z has structural formula (1) and

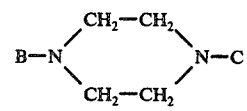 (b)

wherein B & C are each selected for the group consisting of radicals having above structural formula (1), above structural formula (2) and alkyl group having from 1 to 6 carbon atoms with at least one of B & C having structural formula (1).

A water solution of an effective amount of such compound exhibits excellent fabric softening and antistatic properties, e.g. a solution of from 3 to 95 weight percent, preferably from 5 to 40 weight percent.

The alkyloxy hydrocarbons may be either dibasic acids or anhydrides with anhydrides being preferred since the use of anhydrides eliminate secondary reaction products and thus the concomitant removal requirements. Of the anhydrides, maleic and succinic anhydrides are preferred due to the commercial availability thereof.

Preferably, the polyoxyalkylene triamine is reacted with an approximately stoichiometric amount of the alkyloxy hydrocarbon under mild conditions to form the product of the present invention, i.e. a tertiary amino polyoxyalkylene exhibiting excellent substantive and antistatic properties. Temperature and pressure conditions for the reaction are from 80° to 140° C., and 0 to 150 psig., respectively, for a period of 5 to 20 minutes.

EXAMPLES OF THE INVENTION

Operation of the process of the present invention and the formation of fabric softener solutions are described in the following examples which are intended to be merely illustrative and the invention is not to be regarded as limited thereto. The following examples illustrate the preparation of diverse compounds which are dissolved in water to condition cloth samples; the results thereof being set forth in Table I.

EXAMPLE 1

Triethanolamine (13.9 grams) of a commercial grade is introduced into an autoclave together with a 50% aqueous solution of NaOH (1 gram). The water of solution is distilled and the autoclave purged with nitrogen. Ethylene oxide is introduced at a reaction temperature varying between 120° – 125° C. until a total of 300 grams thereof is reacted. The rate of introduction of ethylene oxide is adjusted to maintain the pressure in the autoclave below 20 psig. The molecular weight of the triol is calculated at the end of the reaction to be 3581. The resulting reaction mixture is poured into a beaker with succinic anhydride (26.0 grams) being added with stirring. After ten minutes, the anhydride has reacted to form the estercarboxylic acid derivative as evidenced by the disappearance of the anhydride band in the infrared spectrum at 1785+cm$^{-1}$, and the appearance of the new carbonyl band at 1720 cm$^{-1}$. The reaction product is then cooled, dissolved in 300 ml. of water and stored in a container labelled "A".

EXAMPLE 2

"Tetronic" 707 (200 grams), a commercially available polyoxyalkylene containing two tertiary nitrogen atoms per molecule, having a molecular weight of 2501 to 3000 and having four free hydroxyl groups per molecule is heated with stirring at a temperature of 125° C. with succinic anhydride (25 grams). Stirring is continued for a period of ten minutes at which time all of the anhydride is dissolved and reacted with the polyoxyalkylene compound. The molar ratio of anhydride to free hydroxyl group is 1:1. The resulting product is dissolved in 200 ml. of water and stored in a container labelled "B".

EXAMPLE 3

"Tetronic" 908, having a molecular weight of approximately 4000 and the following molecular structure:

$$\{CH_2 - N = [-(C_3H_6O)_3 - (C_2H_4O)_{16} - H]_2\}_2$$

is reacted with succinic anhydride in accordance with the procedure of Example 2. 300 grams of "Tetronic" 908 is reacted with 30 grams of succinic anhydride with the reaction product being dissolved in 300 ml. of water and stored in a container labelled "C".

EXAMPLE 4

Following the procedures of Example 2, "Tetronic" 1508 (300 grams) is reacted with succinic anhydride (17 grams) to form a reaction product which is dissolved in 200 ml. of water and stored in a container "D". "Tetronic" 1508 has a molecular weight of approximately 7000 and the following structural formula:

$$\{-CH_2 - N = [(C_3H_6O)_6 - (C_2H_4O)_{32} - H]_2\}_2$$

EXAMPLE 5

Piperazine (8.6 grams) and 50% aqueous solution of NaOH (1 gram) is charged into an autoclave together with 100 ml. of p-xylene. The water of solution is evaporated and the vessel purged with nitrogen. Ethylene oxide is introduced at a reaction temperature of 125° C. and at a pressure of 20 psig. until 200 grams of the ethylene oxide is reacted. The calculated molecular weight of the compound is 2086 with each molecule having two free hydroxyl groups. The p-xylene is distilled from the reaction mixture and succinic anhydride (20 grams) is added while stirring for ten minutes at a temperature of 125° C. The resulting reaction product is dissolved in 200 ml. of cold water and stored in a container labelled "E".

EXAMPLE 6

Polyethylene oxide (200 grams) having a molecular weight of 4000 is reacted with succinic anhydride (20 grams) following the procedure of Example 2. The resulting product is dissolved in 200 ml. of water and stored in a container labelled "F".

EXAMPLE 7

"Tetronic" 707 (200 grams) is reacted with maleic anhydride (25 grams) in accordance with the conditions of Example 2. The resulting product is dissolved in 200 ml. of water and stored in a container labelled "G".

EXAMPLE 8

"Tetronic" 707 (200 grams) is reacted with phthalic anhydride (36 grams) following the procedure of Example 2. The resulting reaction product is dissolved in 200 grams of water and stored in a container labelled "H".

EXAMPLE 9

"Tetronic" 1302 (300 grams) having a molecular weight of 6000 and approximately the molecular formula:

$$\{-CH_2 - N = [-(C_3H_6O)_{21} - (C_2H_4O)_7 - H]_2\}_2$$

is reacted with succinic anhydride (20 grams) following the procedures of Example 2. The resulting product is dissolved in 300 ml. of water and stored in a container labelled "I".

The following Table I sets forth the results of the Static Charge Rating (SCR) of the various compounds prepared in accordance with the above Examples together with other commercially available softeners. The various compounds are tested for softening and antistatic effects by adding a 3% water solution to the rinse cycle of an automatic home washing machine, with the resulting washed material being subsequently dried for 45 minutes in an automatic "Kenmore 800" clothes dryer. Each wash load contained 8 lbs. of 2 × 8 inch fabric samples of 65/35 polyester/cotton, 150 denier, broad woven cloth material. After the drying cycle, each load is tested for static cling and rated subjectively for softness as: excellent, good and poor.

The Static Charge Rating (SCR) is determined by brushing each cloth sample 10 times with a nylon felt and placing the brushed cloth sample against an aluminum plate inclined from the horizontal by 60° with the cloth sample being placed on the underside of the plate. The time for each cloth sample to separate from the plate was measured in seconds. A completely untreated fabric of 100% nylon would cling to the aluminum plate for several hours whereas a well treated fabric separated after a few seconds or would not cling at all. The results of the drying and static tests are summarized in the following Table I.

Table I

| COMPOUND | 1 gram soft/8lb. load | | 3 gram soft./8lb. load | |
|---|---|---|---|---|
| | softening rating | SCR test: seconds to separate | softening rating | SCR test: seconds to separate |
| A[1] | poor | 110 | good | 10 (i) |
| A | good | 4 | excellent | 1 |
| B | good | 4 | excellent | 1 |
| C | good | 10 | excellent | 1 |
| D | good | 15 | excellent | 2 |
| E | good | 10 | excellent | 1 |
| F | poor | 125 | good | 10 |
| G | good | 4 | excellent | 1 |
| H | good | 15 | excellent | 3 |
| I | good | 75 | excellent | 7 |
| Carbowax 4000 | poor | 185 | poor | 80 (ii) |
| Adogen 448 | poor | 110 | good | 12 (iii) |
| "HAPS" | poor | 120 | good | 12 (iv) |
| Varisoft 222-90 | poor | 95 | good | 10 (v) |
| none (control) | poor | +1200 | poor | +1200 |

(i) A[1] "Tetronic" 908 not modified
(ii) Carbowax 4000: polyethyleneoxide of MW 4000, sold by Union Carbide
(iii) Adogen 448: ditallow-dimethylammonium chloride
(iv) "HAPS": 3-(N-alkyl -N,N-dimethylammonio)-2-hydroxypropane-1-sulfonate, where the alkyl is a methylene chain of 20 to 22 carbon atoms.
(v) Varisoft 222-90: complex Difatty quarternary sulfate, by Ashland Chemical Co.

While the invention has been described in connection with exemplary embodiments thereof, it will be understood that many modifications will be apparent to those of ordinary skill in the art and that this application is intended to cover any adaptations or variations thereof. Therefore, it is manifestly intended that this invention be only limited by the claims and the equivalents thereof.

I claim:
1. A composition of matter having the following structural formula:

   (a)

wherein X, Y, and Z each being selected from the group consisting of

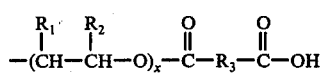   (1)

wherein one of $R_1$ and $R_2$ is hydrogen and the other is an alkyl group having from 1 to 6 carbon atoms with the alkyl to hydrogen mole ratio being less than 0.4 and X being an integer of at least 1 and $R_3$ is a diradical selected for the group consisting of
$R_3$ is a diradical of either:
(a) 1 to 6 methylene groups
(b) a diradical of: —CH=CH—
(c) a diradical of:

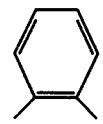

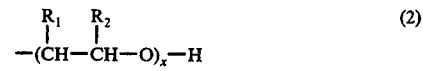   (2)

where $R_1$, $R_2$ and X are as defined above
(3) alkyl radicals having from 1 to 6 carbon atoms

—A—N⟨X Y⟩   (4)

wherein
A is an alkylene radical having from 1 to 6 carbon atoms and X and Y are as defined above
wherein at least one of X, Y and Z has structural formula (1) and

   (b)

wherein B & C are each selected for the group consisting of radicals having above structural formula (1), above structural formula (2) and alkyl group having from 1 to 6 carbon atoms with at least one of B & C having structural formula (1).

2. A fabric softener comprised of a water solution of an effective amount of the compound having the following structural formula:

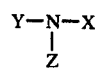   (a)

wherein X, Y, and Z each being selected from the group consisting of

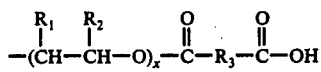   (1)

wherein one of $R_1$ and $R_2$ is hydrogen and the other is an alkyl group having from 1 to 6 carbon atoms with the alkyl to hydrogen mole ratio being less than 0.4 and X being an integer of at least 1 and $R_3$ is a diradical selected for the group consisting of
$R_3$ is a diradical of either:
(a) 1 to 6 methylene groups
(b) a diradical of: —CH=CH—
(c) a diradical of:

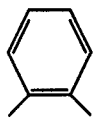

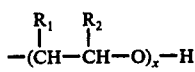   (2)

where $R_1$, $R_2$ and X are as defined above
(3) alkyl radicals having from 1 to 6 carbon atoms

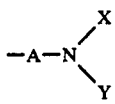   (4)

wherein
A is an alkylene radical having from 1 to 6 carbon atoms and X and Y are as defined above ps wherein at least one of X, Y and Z has structural formula (1) and

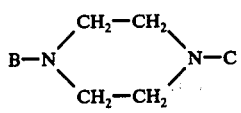   (b)

wherein B & C are each selected for the group consisting of radicals having above structural formula (1), above structural formula (2) and alkyl group having from 1 to 6 carbon atoms with at least one of B & C having structural formula (1).

3. The fabric softener as defined in claim 2 wherein said solution is from 3 to 95 weight percent.

4. The fabric softener as defined in claim 3 wherein said water solution is preferably of from 5 to 40 weight percent.

5. The water softener as defined in claim 4 wherein the water solution is preferably 25 weight percent.

6. A process for preparing a compound having the following structure:

   (a)

wherein X, Y, and Z each being selected from the group consisting of

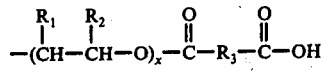   (1)

wherein one of $R_1$ and $R_2$ is hydrogen and the other is an alkyl group having from 1 to 6 carbon atoms with the alkyl to hydrogen mole ratio being less than 0.4 and X being an integer of at least 1 and $R_3$ is a diradical selected for the group consisting of
$R_3$ is a diradical of either:
(a) 1 to 6 methylene groups
(b) a diradical of: —CH=CH—
(c) a diradical of:

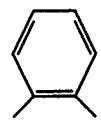

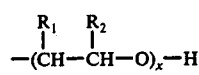   (2)

where $R_1$, $R_2$ and X are as defined above
(3) alkyl radicals having from 1 to 6 carbon atoms

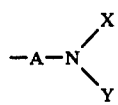   (4)

wherein
A is an alkylene radical having from 1 to 6 carbon atoms and X and Y are as defined above
wherein at least one of X, Y and Z has structural formula (1) and

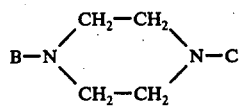   (b)

wherein B & C are each selected for the group consisting of radicals having above structural formula (1), above structural formula (2) and alkyl group having from 1 to 6 carbon atoms with at least one of B & C having structural formula (1), which comprises:
(a) introducing a polyoxyalkylene triamine into a reaction vessel;
(b) introducing an alkyloxy hydrocarbon compound into said reaction vessel;
(c) maintaining the reaction vessel at a temperature of from 80° to 140° C. and at a pressure of from 0 to 150 psigs.; for a period of 5 to 20 minutes; and
(d) withdrawing a reaction product from said reaction vessel.

7. The process as defined in claim 6 wherein said alkyloxy hydrocarbon compound is selected from the group consisting of maleic and succinic anhydrides.

8. The process as defined in claim 6 wherein the temperature is preferably maintained at a temperature of 100° to 120° C.

9. The process as defined in claim 6 wherein the pressure is preferably maintained at 0 psig.

10. The process for treating fabrics to improve the antistatic properties thereof, which comprises:
   (a) forming a water solution of an effective amount of the compound having the following structural formula:

 (a)

wherein X, Y, and Z each being selected from the group consisting of

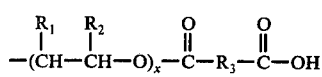 (1)

wherein one of $R_1$ and $R_2$ is hydrogen and the other is an alkyl group having from 1 to 6 carbon atoms with the alkyl to hydrogen mole ratio being less than 0.4 and X being an integer of at least 1 and $R_3$ is a diradical selected for the group consisting of $R_3$ is a diradical of either:
   (a) 1 to 6 methylene groups
   (b) a diradical of: —CH=CH—
   (c) a diradical of:

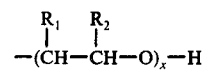 (2)

where $R_1$, $R_2$ and X are as defined above
   (3) alkyl radicals having from 1 to 6 carbon atoms

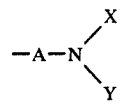 (4)

wherein
   A is an alkylene radical having from 1 to 6 carbon atoms and X and Y are as defined above
wherein at least one of X, Y and Z has structural formula (1) and

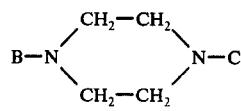 (b)

wherein B & C are each selected for the group consisting of radicals having above structural formula (1), above structural formula (2) and alkyl group having from 1 to 6 carbon atoms with at least one of B & C having structural formula (1);
   (b) introducing the solution of step (a) into a washing zone including said fabrics; and
   (c) drying the thus treated fabrics of step b).

11. The process as defined in claim 10 wherein said water solution is added to said washing zone during a rinse cycle thereof.

* * * * *